US012758267B2

(12) United States Patent
McClintock

(10) Patent No.: US 12,758,267 B2
(45) Date of Patent: Oct. 13, 2026

(54) MODULAR HEAD FOR PEDICLE SCREW

(71) Applicant: K2M, Inc., Leesburg, VA (US)

(72) Inventor: Larry E. McClintock, Gore, VA (US)

(73) Assignee: VB Spine LLC, Sterling, VA (US)

( * ) Notice: Subject to any disclaimer, the term of this patent is extended or adjusted under 35 U.S.C. 154(b) by 37 days.

(21) Appl. No.: 18/294,746

(22) PCT Filed: Aug. 4, 2022

(86) PCT No.: PCT/US2022/039395
§ 371 (c)(1),
(2) Date: Feb. 2, 2024

(87) PCT Pub. No.: WO2023/022886
PCT Pub. Date: Feb. 23, 2023

(65) Prior Publication Data

US 2024/0341817 A1 Oct. 17, 2024

Related U.S. Application Data

(60) Provisional application No. 63/297,856, filed on Jan. 10, 2022, provisional application No. 63/234,356, filed on Aug. 18, 2021.

(51) Int. Cl.
*A61B 17/70* (2006.01)

(52) U.S. Cl.
CPC ...... *A61B 17/7034* (2013.01); *A61B 17/7038* (2013.01)

(58) Field of Classification Search
CPC ............ A61B 17/7038; A61B 17/7037; A61B 17/7034
See application file for complete search history.

(56) References Cited

U.S. PATENT DOCUMENTS

| | | | |
|---|---|---|---|
| 856,265 | A | 6/1907 | Kunkle |
| 5,382,248 | A | 1/1995 | Jacobson et al. |

(Continued)

FOREIGN PATENT DOCUMENTS

| | | | |
|---|---|---|---|
| EP | 2873383 | A1 | 5/2015 |
| WO | 2018023030 | A1 | 2/2018 |
| WO | 2020056385 | A1 | 3/2020 |

OTHER PUBLICATIONS

International Search Report for PCT/US2021/039063 dated Oct. 13, 2021. (2 pages).

(Continued)

*Primary Examiner* — David W Bates
(74) *Attorney, Agent, or Firm* — Lerner David LLP

(57) ABSTRACT

A spinal fixation device includes a modular head assembly and a bone screw having a head and a shank. The modular head assembly includes: a housing defining a throughhole from a proximal surface to a distal surface of the housing; an anvil slidable within the throughhole; a washer; an assembly cap secured to the housing; a first biasing member arranged to bias the anvil toward the proximal surface of the washer; a retaining ring positioned at least partially within the cavity of the assembly cap; and a second biasing member arranged to bias the retaining ring toward the second portion of the assembly cap. Movement of the retaining ring from a first portion of the assembly cap to a second portion of the assembly cap compresses the retaining ring from a neutral configuration to a compressed configuration thereby securing the bone screw relative to the housing.

15 Claims, 12 Drawing Sheets

(56) References Cited

U.S. PATENT DOCUMENTS 5,487,744 A 1/1996 Howland
5,549,608 A 8/1996 Errico et al.
5,554,157 A 9/1996 Errico et al.
5,575,972 A 11/1996 Mitsuhashi et al.
5,578,033 A 11/1996 Errico et al.
5,584,834 A 12/1996 Errico et al.
5,586,984 A 12/1996 Errico et al.
5,609,593 A 3/1997 Errico et al.
5,609,594 A 3/1997 Errico et al.
5,669,911 A 9/1997 Errico et al.
5,725,528 A 3/1998 Errico et al.
5,733,285 A 3/1998 Errico et al.
5,735,851 A 4/1998 Errico et al.
5,800,435 A 9/1998 Errico et al.
5,817,094 A 10/1998 Errico et al.
6,004,322 A 12/1999 Bernstein
6,050,997 A 4/2000 Mullane
6,146,383 A 11/2000 Studer et al.
6,280,442 B1 8/2001 Barker et al.
6,482,207 B1 11/2002 Errico
6,623,485 B2 9/2003 Doubler et al.
6,660,004 B2 12/2003 Barker et al.
6,669,697 B1 12/2003 Pisharodi
6,733,502 B2 5/2004 Altarac et al.
6,837,889 B2 1/2005 Shluzas
6,869,433 B2 3/2005 Glascott
6,887,242 B2 5/2005 Doubler et al.
7,066,937 B2 6/2006 Shluzas
7,087,057 B2 8/2006 Konieczynski et al.
7,144,396 B2 12/2006 Shluzas
7,186,255 B2 3/2007 Baynham et al.
7,306,606 B2 12/2007 Sasing
7,314,467 B2 1/2008 Howland
7,322,981 B2 1/2008 Jackson
7,662,175 B2 2/2010 Jackson
7,682,377 B2 3/2010 Konieczynski et al.
7,722,645 B2 5/2010 Bryan
7,727,261 B2 6/2010 Barker et al.
7,749,258 B2 7/2010 Biedermann et al.
7,766,943 B1 8/2010 Fallin et al.
7,766,945 B2 8/2010 Nilsson et al.
7,776,067 B2 8/2010 Jackson
7,785,354 B2 8/2010 Biedermann et al.
7,789,896 B2 9/2010 Jackson
7,833,250 B2 11/2010 Jackson
7,842,073 B2 11/2010 Richelsoph et al.
7,879,075 B2 2/2011 Shluzas
7,901,435 B2 3/2011 Slivka et al.
7,942,909 B2 5/2011 Hammill, Sr. et al.
7,942,910 B2 5/2011 Doubler et al.
7,942,911 B2 5/2011 Doubler et al.
7,947,065 B2 5/2011 Hammill, Sr. et al.
7,951,172 B2 5/2011 Chao et al.
7,951,173 B2 5/2011 Hammill, Sr. et al.
8,007,518 B2 8/2011 Winslow et al.
8,012,181 B2 9/2011 Winslow et al.
8,016,861 B2 9/2011 Mitchell et al.
8,048,115 B2 11/2011 Winslow et al.
8,048,126 B2 11/2011 Altarac et al.
8,048,133 B2 11/2011 Biedermann et al.
8,052,724 B2 11/2011 Jackson
8,057,515 B2 11/2011 Flynn et al.
8,057,519 B2 11/2011 Justis et al.
8,066,744 B2 11/2011 Justis et al.
8,075,603 B2 12/2011 Hammill, Sr. et al.
8,083,772 B2 12/2011 Winslow et al.
8,083,775 B2 12/2011 Winslow et al.
8,083,777 B2 12/2011 Butters et al.
8,088,152 B2 1/2012 Schumacher
8,092,501 B2 1/2012 Mitchell et al.
8,092,504 B2 1/2012 Warnick
8,097,024 B2 1/2012 Winslow et al.
8,097,025 B2 1/2012 Hawkes et al.
8,100,946 B2 1/2012 Strausbaugh et al.
8,114,134 B2 2/2012 Winslow et al.
8,133,262 B2 3/2012 Whipple
8,137,384 B2 3/2012 Heiges et al.
8,137,386 B2 3/2012 Jackson
8,142,481 B2 3/2012 Warnick
8,147,522 B2 4/2012 Warnick
8,167,912 B2 5/2012 Jacofsky et al.
8,172,876 B2 5/2012 Janowski et al.
8,192,468 B2 6/2012 Biedermann et al.
8,192,470 B2 6/2012 Biedermann et al.
8,197,518 B2 6/2012 Hammill, Sr. et al.
8,211,155 B2 7/2012 Winslow et al.
8,216,281 B2 7/2012 Winslow et al.
8,221,471 B2 7/2012 Kovach et al.
8,257,397 B2 9/2012 Winslow et al.
8,267,969 B2 9/2012 Altarac et al.
8,298,265 B2 10/2012 Purcell et al.
8,298,274 B2 10/2012 Barker, Jr. et al.
8,333,792 B2 12/2012 Winslow et al.
8,337,530 B2 12/2012 Hestad et al.
8,337,536 B2 12/2012 Mitchell et al.
8,372,122 B2 2/2013 Winslow et al.
8,394,127 B2 3/2013 Winslow et al.
8,398,689 B2 3/2013 Abdou
8,430,916 B1 4/2013 Winslow et al.
8,444,681 B2 5/2013 Jackson et al.
8,465,530 B2 6/2013 Hammill, Sr. et al.
8,475,501 B2 7/2013 Jackson
8,506,609 B2 8/2013 Biedermann et al.
8,506,611 B2 8/2013 Biedermann et al.
8,518,085 B2 8/2013 Winslow et al.
8,529,604 B2 9/2013 Barker, Jr. et al.
8,556,938 B2 10/2013 Jackson et al.
8,562,652 B2 10/2013 Biedermann et al.
8,617,217 B2 12/2013 Iott et al.
8,628,558 B2 1/2014 Harvey et al.
8,636,769 B2 1/2014 Jackson
8,636,781 B2 1/2014 Biedermann et al.
8,636,782 B2 1/2014 Biedermann et al.
8,663,288 B2 3/2014 Konieczynski et al.
8,663,290 B2 3/2014 Doubler et al.
8,663,291 B2 3/2014 Doubler et al.
8,685,064 B2 4/2014 Hestad et al.
8,709,050 B2 4/2014 Shluzas
8,758,410 B2 6/2014 Heiges et al.
8,764,810 B2 7/2014 Biedermann et al.
8,814,911 B2 8/2014 Jackson
8,845,700 B2 9/2014 Kwak et al.
8,870,927 B2 10/2014 Matthis et al.
8,881,358 B2 11/2014 Biedermann et al.
8,888,827 B2 11/2014 Harper et al.
8,900,270 B2 12/2014 Fauth et al.
8,900,272 B2 12/2014 Jackson
8,926,671 B2 1/2015 Biedermann et al.
8,940,024 B2 1/2015 Biedermann et al.
8,961,568 B2 2/2015 McKinley et al.
8,979,904 B2 3/2015 Jackson et al.
8,986,349 B1 3/2015 German et al.
8,992,579 B1 3/2015 Gustine et al.
8,998,958 B2 4/2015 Dauster et al.
8,998,959 B2 4/2015 Jackson et al.
8,998,960 B2 4/2015 Jackson
8,998,965 B2 * 4/2015 Biedermann ...... A61B 17/7038
606/279
8,998,967 B2 4/2015 Biedermann et al.
9,005,259 B2 4/2015 Biedermann et al.
9,017,390 B2 4/2015 Biedermann et al.
9,023,086 B2 5/2015 Biedermann et al.
9,044,273 B2 6/2015 Richelsoph et al.
9,060,814 B2 6/2015 Doubler et al.
9,066,759 B2 6/2015 Biedermann et al.
9,119,674 B2 9/2015 Matthis et al.
9,131,971 B2 9/2015 Biedermann et al.
9,144,444 B2 9/2015 Jackson
9,155,567 B2 10/2015 Auerbach et al.
9,173,684 B2 11/2015 Biedermann et al.
9,186,187 B2 11/2015 Mishra
9,198,694 B2 12/2015 Mishra et al.
9,198,695 B2 12/2015 Shluzas et al.
9,232,969 B2 1/2016 Farris

(56) References Cited

U.S. PATENT DOCUMENTS 9,247,965 B2 2/2016 Biedermann et al.
9,254,150 B2 2/2016 Biedermann et al.
9,277,938 B2 3/2016 Biedermann et al.
9,277,941 B2 3/2016 Biedermann et al.
9,277,942 B2 3/2016 Biedermann et al.
9,289,244 B2 3/2016 Hestad et al.
9,289,246 B2 3/2016 Biedermann et al.
9,333,016 B2 5/2016 Biedermann et al.
9,333,017 B2 5/2016 Biedermann et al.
9,339,304 B2 5/2016 Biedermann et al.
9,339,320 B2 5/2016 Heiges et al.
9,351,766 B2 5/2016 Biedermann et al.
9,358,047 B2 6/2016 Mishra et al.
9,364,266 B2 6/2016 Biedermann et al.
9,439,680 B2 9/2016 Biedermann et al.
9,451,990 B2 9/2016 Fauth et al.
9,451,991 B2 9/2016 Raju et al.
9,452,006 B2 9/2016 Biedermann et al.
9,453,526 B2 9/2016 Black et al.
9,463,047 B2 10/2016 Raju et al.
9,463,049 B2 10/2016 Konieczynski et al.
9,480,517 B2 11/2016 Jackson et al.
9,486,245 B2 11/2016 Matthis et al.
9,486,246 B2 11/2016 Biedermann et al.
9,492,204 B2 11/2016 Biedermann et al.
9,510,868 B2 12/2016 Biedermann et al.
9,522,021 B2 12/2016 Jackson et al.
9,532,809 B2 1/2017 Biedermann et al.
9,532,810 B2 1/2017 Hestad et al.
9,549,763 B2 1/2017 Harper et al.
9,572,600 B2 2/2017 Biedermann et al.
9,579,125 B2 2/2017 Raju et al.
9,597,119 B2 3/2017 Jackson et al.
9,603,630 B2 3/2017 Farris
9,603,635 B2 3/2017 Leff et al.
9,615,858 B2 4/2017 Doubler et al.
9,649,139 B2 5/2017 Sharifi-Mehr et al.
9,649,142 B2 5/2017 Doubler et al.
9,693,808 B2 7/2017 Fauth et al.
9,707,013 B2 7/2017 Rezach et al.
9,737,338 B2 8/2017 Bazille
9,763,700 B1 9/2017 Gregory
9,788,865 B2 10/2017 Matthis et al.
9,820,780 B2 11/2017 Duncan et al.
9,839,446 B2 12/2017 Biedermann et al.
9,848,916 B2 12/2017 Biedermann et al.
9,883,892 B2 2/2018 Jackson et al.
9,895,170 B2 2/2018 Biedermann et al.
9,895,171 B2 2/2018 Webb
9,907,574 B2 3/2018 Jackson et al.
9,918,745 B2 3/2018 Jackson et al.
9,924,971 B2 * 3/2018 Biedermann ...... A61B 17/8615
9,924,975 B2 * 3/2018 Jackson ............. A61B 17/7037
9,936,983 B2 4/2018 Mesiwala et al.
9,949,763 B2 4/2018 Rezach
9,949,765 B2 4/2018 Nichols et al.
9,956,003 B2 * 5/2018 Prevost .............. A61B 17/7035
9,956,006 B2 5/2018 Jackson
9,962,193 B2 5/2018 Biedermann et al.
9,980,753 B2 5/2018 Jackson et al.
10,022,158 B2 7/2018 Biedermann et al.
10,058,367 B2 8/2018 Biedermann et al.
10,064,659 B2 9/2018 Biedermann et al.
10,076,363 B2 9/2018 Biedermann et al.
10,130,395 B2 11/2018 Leff et al.
10,136,924 B2 11/2018 Konieczynski et al.
10,159,519 B2 12/2018 Biedermann et al.
10,182,848 B2 1/2019 Biedermann et al.
10,188,432 B2 1/2019 Jackson et al.
10,238,430 B2 3/2019 Jackson et al.
10,258,383 B2 4/2019 Biedermann et al.
10,258,384 B2 4/2019 Gregory
10,285,738 B1 * 5/2019 Doubler ............. A61B 17/7037
10,335,204 B2 7/2019 Matthis et al.
10,357,287 B2 7/2019 Schlaepfer et al.
10,363,073 B2 7/2019 Raina et al.
10,368,916 B2 8/2019 May
10,383,662 B2 8/2019 Biedermann et al.
10,478,229 B2 11/2019 Jackson et al.
10,568,667 B2 2/2020 Biester et al.
10,716,609 B2 7/2020 Biedermann et al.
10,722,272 B2 7/2020 Biedermann et al.
10,729,483 B2 8/2020 Biedermann et al.
10,779,862 B2 9/2020 Biedermann et al.
10,799,272 B2 10/2020 Jackson
10,813,672 B2 10/2020 Jackson et al.
10,856,909 B2 12/2020 Jackson et al.
10,856,911 B2 12/2020 Jackson et al.
10,869,694 B2 12/2020 Jackson et al.
10,918,420 B2 2/2021 Jackson et al.
10,945,768 B2 3/2021 Jackson et al.
10,966,759 B2 4/2021 Gregory
10,980,574 B2 4/2021 Konieczynski et al.
10,987,137 B2 4/2021 Jackson et al.
11,020,150 B1 * 6/2021 Doubler ............. A61B 17/7032
11,026,723 B2 * 6/2021 Rezach .................. B33Y 80/00
11,090,090 B2 8/2021 Biedermann et al.
11,123,109 B2 9/2021 Biedermann et al.
11,147,597 B2 10/2021 Jackson
11,160,582 B2 11/2021 Biedermann et al.
11,219,470 B2 1/2022 Avidano et al.
11,333,192 B1 * 5/2022 Lentner ................. F16C 11/069
12,114,898 B2 * 10/2024 McClintock ....... A61B 17/7038
12,414,801 B2 * 9/2025 Jackson ............. A61B 17/7037
2003/0060823 A1 3/2003 Bryan
2004/0097933 A1 5/2004 Lourdel et al.
2006/0200131 A1 9/2006 Chao et al.
2007/0055242 A1 3/2007 Bailly
2007/0088357 A1 4/2007 Johnson et al.
2007/0090238 A1 4/2007 Justis
2008/0262556 A1 10/2008 Jacofsky et al.
2010/0125302 A1 5/2010 Hammill, Sr. et al.
2010/0137920 A1 6/2010 Hammill, Sr. et al.
2010/0198272 A1 8/2010 Keyer et al.
2010/0305621 A1 12/2010 Wang et al.
2011/0118783 A1 5/2011 Winslow et al.
2011/0307018 A1 12/2011 Zucherman et al.
2012/0041490 A1 2/2012 Jacob et al.
2013/0012954 A1 1/2013 Paroth et al.
2013/0046345 A1 2/2013 Jones et al.
2013/0110180 A1 5/2013 Doubler et al.
2013/0150852 A1 * 6/2013 Shluzas .............. A61B 17/7032 606/65
2014/0046374 A1 2/2014 Asaad et al.
2014/0257411 A1 * 9/2014 Rezach .............. A61B 17/7037 606/305
2014/0343617 A1 11/2014 Hannen
2015/0196337 A1 7/2015 Biedermann et al.
2015/0196338 A1 7/2015 Biedermann et al.
2015/0201972 A1 7/2015 Doubler et al.
2015/0250512 A1 9/2015 Poker et al.
2015/0282844 A1 * 10/2015 Vedula ............... A61B 17/8625 606/305
2016/0030086 A1 2/2016 Mishra
2016/0030090 A1 2/2016 Webb
2016/0220277 A1 8/2016 Rezach et al.
2016/0262801 A1 9/2016 Rezach et al.
2017/0020574 A1 1/2017 Biedermann et al.
2017/0049482 A1 2/2017 Campbell et al.
2017/0049484 A1 2/2017 Leff et al.
2017/0065306 A1 3/2017 Fauth et al.
2017/0112542 A1 4/2017 Biedermann et al.
2017/0172630 A1 6/2017 Biedermann et al.
2017/0224386 A1 8/2017 Leff et al.
2017/0245898 A1 8/2017 May et al.
2017/0265903 A1 9/2017 Longtain et al.
2017/0333085 A1 11/2017 Jackson et al.
2018/0014858 A1 1/2018 Biester et al.
2018/0014862 A1 1/2018 Raina et al.
2018/0014863 A1 1/2018 Biester et al.
2018/0021068 A1 1/2018 May et al.
2018/0036039 A1 2/2018 Biedermann et al.
2018/0055545 A1 3/2018 Biedermann et al.
2018/0092679 A1 4/2018 Toon et al.

(56) References Cited

U.S. PATENT DOCUMENTS

| | | | | |
|---|---|---|---|---|
| 2018/0110548 | A1 | 4/2018 | May et al. | |
| 2018/0116696 | A1 | 5/2018 | Hammer et al. | |
| 2018/0325569 | A1* | 11/2018 | Ramsay | A61B 17/7037 |
| 2019/0110817 | A1 | 4/2019 | Shluzas et al. | |
| 2019/0150989 | A1 | 5/2019 | Biester et al. | |
| 2020/0038075 | A1* | 2/2020 | Barrus | A61B 17/70 |

OTHER PUBLICATIONS

International Search Report issued in Appln. No. PCT/US2021/059376 mailed Feb. 3, 2022 (2 pages).

European Search Report issued in Appln. No. 21217539.2 dated Jun. 10, 2022 (2 pages).

International Search Report issued in Appln. No. PCT/US2022/039395 mailed Jan. 31, 2023 (4 pages).

Extended European Search Report including Search Opinion from 21828986.6, dated Jun. 14, 2024, pp. 1-5.

Extended European Search Report issued in Appln. No. 25160819.6 dated May 7, 2025 (10 pages).

* cited by examiner

MODULAR HEAD FOR PEDICLE SCREW

CROSS-REFERENCE TO RELATED APPLICATIONS

The present application is a national phase entry under 35 U.S.C. § 371 of International Application No. PCT/US2022/039395, filed Aug. 4, 2022, published in English, which claims priority to U.S. Provisional Application No. 63/297,856, filed Jan. 10, 2022, and U.S. Provisional Application No. 63/234,356, filed Aug. 18, 2021, the disclosures of which are incorporated herein by reference.

BACKGROUND OF THE INVENTION

The present disclosure relates to spinal fixation devices and, more particularly, to modular pedicle fixation assemblies.

The spinal column is a complex system of bones and connective tissues that provides support for the body while protecting the spinal cord and nerves. The spinal column includes a series of vertebral bodies stacked on top of one another, each vertebral body including an inner or central portion of relatively weak cancellous bone and an outer portion of relatively strong cortical bone. Situated between each vertebral body is an intervertebral disc that cushions and dampens compressive forces exerted upon the spinal column, as well as maintains proper spacing of the bodies with respect to each other. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine) and spondylolisthesis (forward displacement of one vertebra over another, usually in a lumbar or cervical spine), for example, that are caused by abnormalities, such as disease or trauma, and that are characterized by misalignment of the spinal column. When the spinal column is misaligned, one or more of the misaligned vertebral bodies can "pinch" or apply pressure to the underlying spinal cord and nerves, which often results in debilitating pain and diminished nerve function. For this reason, the forgoing conditions regularly require the imposition and/or maintenance of corrective forces on the spine in order to return the spine to its normal alignment.

A surgical technique, commonly referred to as spinal fixation, utilizes surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column.

One common spinal fixation device utilizes spinal rods placed generally parallel to the spine and fixation devices, such as pedicle screw assemblies, interconnected between the spinal rods and selected portions of the spine. In some instances, the spinal rods can then be connected to each other via cross-connecting members to provide a more rigid support and alignment system.

Pedicle screw assemblies typically include a bone screw and a housing or coupling element for coupling the bone screw to the spinal rod. Pedicle screws generally come in two forms: a polyaxial pedicle screw (which allows the housing to freely rotate relative to the head of the screw) and a uniplanar pedicle screw (which restricts movement of the housing relative to the screw head to a single plane).

Conventional pedicle screws are "top loaded" meaning that to assemble the pedicle screw, a shank of the bone screw must be inserted into a proximal end of the housing until the head of the bone screw is retained within the housing and the shank extends from a distal end of the housing. Thus, when securing a conventional pedicle screw to bone, the surgeon must thread the screw into bone while the head of the screw is positioned within the housing.

Despite the improvements that have been made to spinal fixation devices, various drawbacks remain. For example, the housing of a conventional "top loaded" pedicle screw assembly can obstruct a surgeon's vision and/or access while performing operative tasks such as decortication and decompression. This problem is exacerbated by the fact that the housing is subject to "flop" (e.g., unwanted movement) around the head of the screw, which can complicate handling of the pedicle screw assembly, alignment of the housing, and fastening of the pedicle screw assembly to bone. Moreover, a surgeon may find it desirable to select between a polyaxial and a uniplanar pedicle screw, based upon various intraoperative considerations, after the screw has been secured to bone. However, switching from a conventional "top loaded" polyaxial pedicle screw to a conventional "top loaded" uniplanar pedicle screw (or vice-versa), after implantation, is not desirable because it requires removal of the previously implanted pedicle screw which can weaken the bone.

BRIEF SUMMARY OF THE INVENTION

A "bottom loaded" or "modular" pedicle screw assembly is provided herein. Among other advantages, the distal end of the modular head assembly is configured to receive the head of the bone screw after the screw has been secured to bone. As a result, the surgeon's vision and access is not impaired while performing necessary operative tasks. Moreover, the bone screw defines a feature(s), such as a notch(es), designed to selectively engage a corresponding feature, such as a protrusion, provided on select modular head assemblies to restrict movement of the modular head assembly to a single plane relative to the bone screw. Put another way, a kit of differently configured modular head assemblies can include at least one first modular head assembly without the corresponding feature (e.g., the protrusion) and at least one second modular head assembly provided with the corresponding feature. In this manner, a surgeon can select and secure one of the first or second modular head assemblies to the bone screw to create a polyaxial or uniplanar pedicle screw after the bone screw has been implanted into bone and without necessitating removal of the screw from bone. Furthermore, the first and second modular housings may include biasing members, such as wave springs, that provide a constant biasing force to the head of the bone screw and prevent the housing from "flopping" on the screw head which improves handling and alignment of the modular pedicle screw.

One embodiment of the spinal fixation device includes a modular head assembly and a bone screw including a head and a shank extending from the head. The modular head assembly includes: a housing having a proximal surface, a distal surface, and a throughhole formed through the housing from the proximal surface to the distal surface; an anvil slidable within a portion of the throughhole; a washer disposed within the throughhole of the housing, the washer having a proximal surface, a distal surface, and an aperture extending through the washer from the proximal surface to the distal surface, the aperture sized to receive the head of the bone screw therethrough; an assembly cap secured to the housing, the assembly cap including an inner surface defining a cavity having a first portion and a second portion, the first portion having a first diameter and the second portion having a second diameter smaller than the first diameter; a first biasing member arranged to bias the anvil toward the proximal surface of the washer; a retaining ring positioned at least partially within the cavity of the assembly cap, the retaining ring transitionable between a first configuration in which the retaining ring is sized to receive the head of the bone screw and a second configuration in which the retaining ring is compressed about the bone screw; and a second biasing member arranged to bias the retaining ring toward the second portion of the assembly cap. Movement of the retaining ring from the first portion of the assembly cap to the second portion of the assembly cap compresses the retaining ring from the first configuration to the second configuration and secures the bone screw relative to the housing.

In another embodiment, a method of assembling a spinal fixation device is provided. The method includes: providing a housing having a proximal portion adjacent a proximal surface, a distal portion adjacent a distal surface, and a throughhole formed through the housing from the proximal surface to the distal surface defining first and second annular faces; sliding an anvil into the throughhole to bias a first biasing member between the first annular face and a portion of the anvil; placing a washer within the throughhole such that the washer is located distal of the anvil; inserting a resilient retaining ring at least partially into an assembly cap, the assembly including an inner surface defining a cavity having a first portion with a first diameter and a second portion with a second diameter smaller than the first diameter; and securing the assembly cap to the housing, thereby fixing the washer against the second annular face and compressing a second biasing member to bias the retaining ring toward the second portion of the assembly cap.

In a further embodiment, a spinal fixation kit is provided. The spinal fixation kit includes: a bone screw having a head and a shank, the head defining at least one notch; a first modular head assembly and a second modular head assembly. The first modular head assembly includes: a first housing having a first proximal surface, a first distal surface, and a first throughhole formed through the housing from the first proximal surface to the first distal surface; and a first anvil disposed within the first throughhole, the first anvil being shaped such that when the first housing receives the head of the bone screw, the first housing is permitted to move about the head of the bone screw in multiple axis. The second modular head assembly includes: a second housing having a second proximal surface, a second distal surface, and a second throughhole formed through the housing from the first proximal surface to the first distal surface; and a second anvil disposed within the second throughhole, the second anvil including a protrusion sized to be received by the at least one notch of the bone screw to restrict relative movement between the second housing and the bone screw to a single plane. In this regard, a clinician can select and secure one of the first or second modular head assemblies to the bone screw to create a polyaxial or uniplanar pedicle screw after the bone screw has been implanted into bone and without necessitating removal of the screw from bone.

DETAILED DESCRIPTION

As used herein, when referring to the modular pedicle screw assembly, the term "proximal" means the portion of the assembly or a component thereof that is closer to the clinician and the term "distal" means the portion of the assembly or a component thereof that is furthest from the clinician. Also, as used herein, the terms "substantially,"

"generally." and "about" are intended to mean that slight deviations from absolute are included within the scope of the term so modified.

Figure 1A:
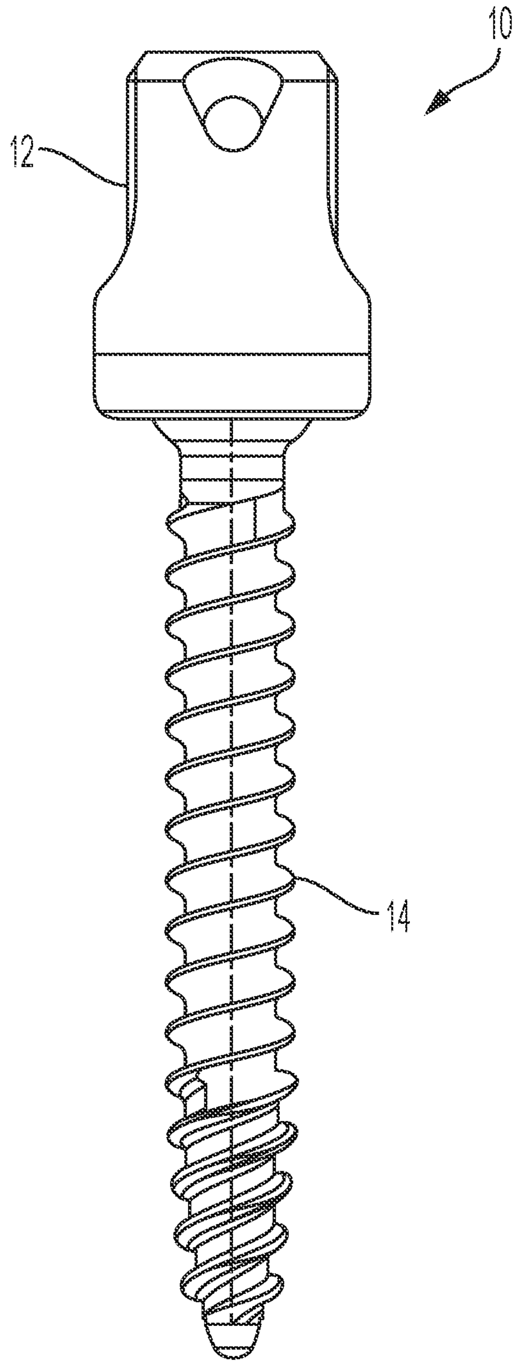
FIG. 1A is a side elevation view of a modular pedicle screw including a bone screw and modular head assembly according to an embodiment of the present disclosure.
Figure 1B:
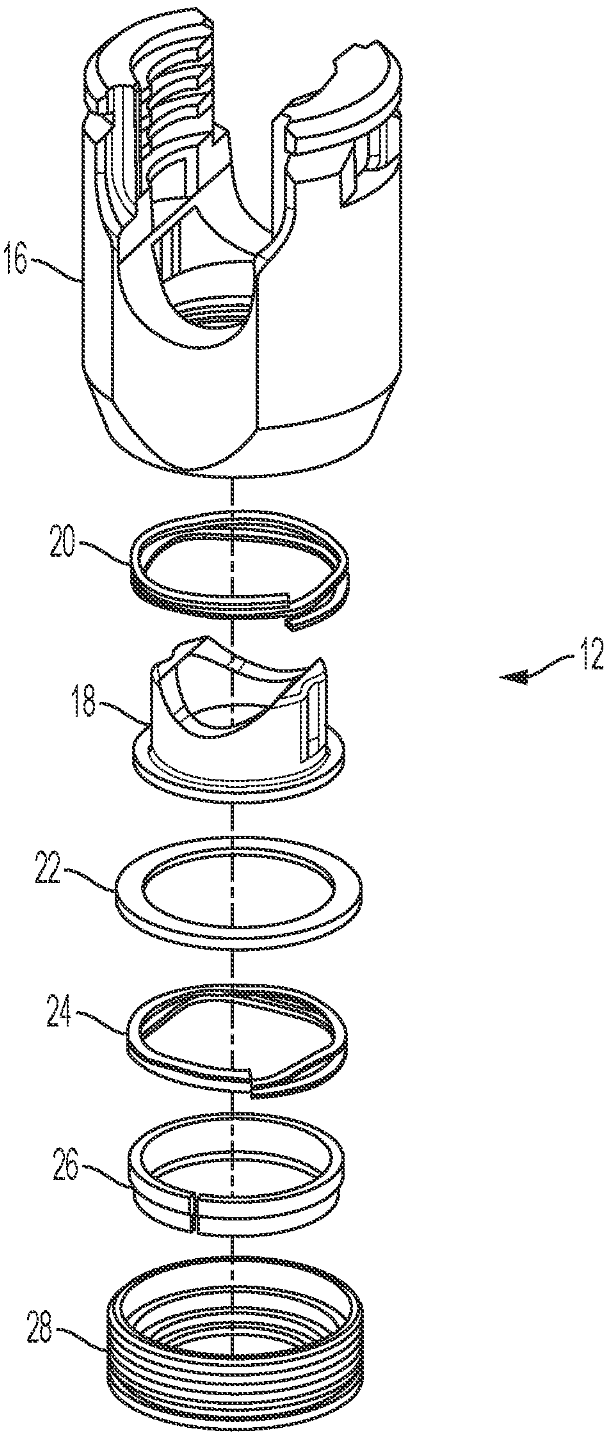
FIG. 1B is an exploded view of the modular head assembly of FIG. 1A.

FIGS. 1A and 1B illustrate a modular pedicle screw assembly 10 in accordance with an embodiment of the present disclosure. Pedicle screw 10 includes a modular head assembly 12 and a bone screw 14. Modular head assembly 12 is designed such that bone screw 14 can be "bottom loaded" or passed through a distal end of the modular head assembly and fastened to the bone screw after the screw has been implanted in bone.

With specific reference to FIG. 1B, modular head assembly 12 includes a housing 16, one of a polyaxial anvil 18*a* (FIGS. 6A-6C) or a uniplanar anvil 18*b* (FIGS. 7A-7C), a first biasing member 20 circumferentially surrounding the anvil, a washer 22, a second biasing member 24, a retaining ring 26 for fixing the rotational and angular position of the bone screw relative to the housing, and an assembly cap 28 for securing the anvil, the first and second biasing members, the washer and the retaining ring within the housing. Unless a structural or functional distinction between polyaxial anvil 18*a* and uniplanar anvil 18*b* is being described, the anvil is generally referred to below as anvil 18.

Figure 2A:
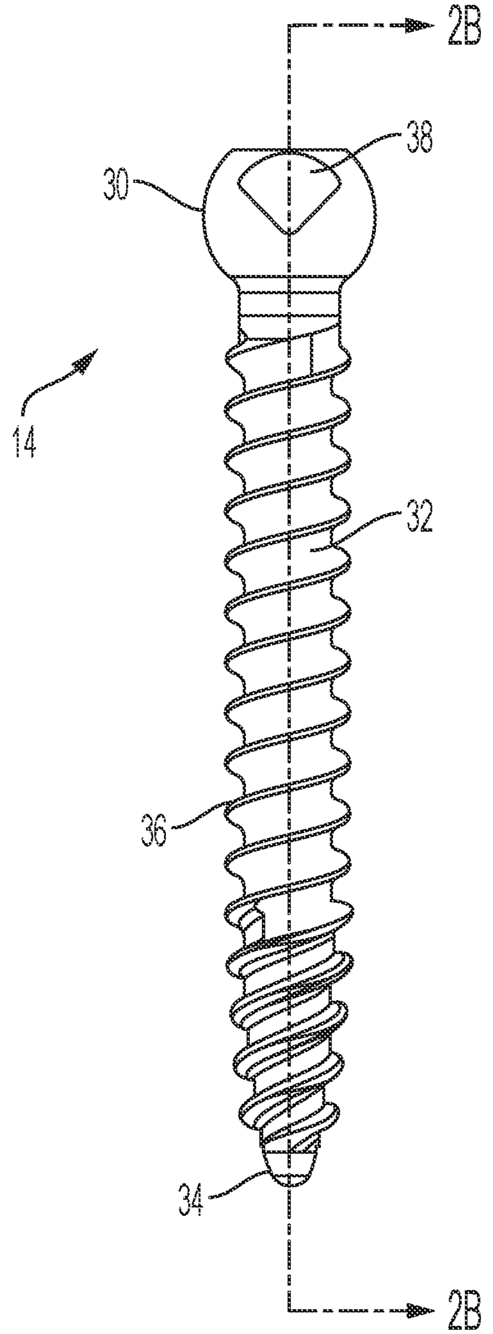
FIG. 2A is a side elevation view of the bone screw of FIG. 1A.
Figure 2B:
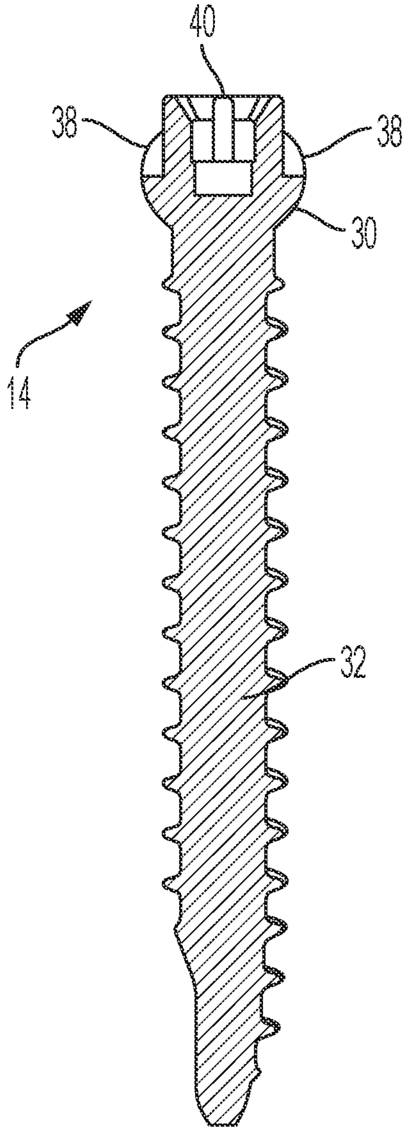
FIG. 2B is a cross section view of the bone screw of FIG. 2A taken along line 2B-2B.

Referring to FIGS. 2A and 2B, bone screw 14 includes a head 30 provided at a proximal end thereof and a shank 32 extending from the head along an axis. Shank 32 is formed as an elongated body and extends from a distal tip 34 to a proximal end that is coupled (e.g., monolithically formed) to head 30. Distal tip 34 is generally conically-shaped to facilitate insertion of the screw 14 into bone and, in some embodiments, may be self-starting. The elongated body of shank 32 may have a substantially uniform outer diameter upon which a helical thread 36 is provided that allows bone screw 14 to be threadably inserted and retained within bone. Helical thread 36 may be continuous or discontinuous, of uniform or non-uniform pitch, single threaded or double threaded and self-tapping or non-self-tapping depending upon the needs of the procedure being performed. It is also contemplated to include cutting flutes to facilitate implantation into bone. In some embodiments, bone screw 14 may be cannulated to permit the passage of a guide wire (not shown) or other instrumentation therethrough. In embodiments in which bone screw 14 defines a cannulation, fenestrations (not shown) may be formed through an outer surface of shank 32 and into communication with the cannulation. Such a design may permit the introduction of bone cement or the like after implantation of the screw within bone.

The head 30 of bone screw 14 is generally spherical in shape with at least one notch 38 designed to engage a corresponding feature(s), such as a protrusion(s), provided on uniplanar anvil 18*b* (but not polyaxial anvil 18*a*) to selectively restrict movement of the uniplanar modular head assembly to a single plane relative to the bone screw. Put another way, a modular head assembly encompassing a polyaxial anvil 18*a* (e.g., an anvil without the corresponding protrusion), permits the polyaxial modular head assembly to freely rotate (e.g., move in multiple axis) about the generally spherical head 30 of bone screw 14. On the other hand, when utilizing a modular head assembly 12 encompassing a uniplanar anvil 18*b*, the protrusion(s) of the uniplanar anvil protrude into the notch(es) 38 of bone screw 14 and restricts movement of modular head assembly 12 to a single plane when the modular head assembly is secured to the bone screw.

As shown in FIG. 2B, the proximal portion of the head 30 of bone screw 14 defines a tool engaging recess 40 configured to receive a driving tool (not shown). Tool engaging recess 40 may be any suitable shape capable of transmitting a rotational motion of the tool to the head 30 of bone screw 14. In one non-limiting embodiment, tool engaging recess 38 may be a hexalobe, as described in U.S. Pat. No. 9,649,139, which is incorporated herein in reference in its entirety.

Figure 3A:
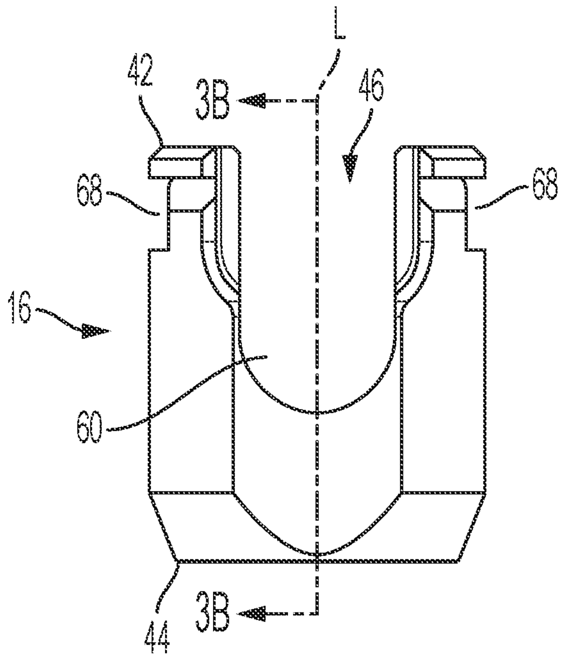
FIG. 3A is a side elevation view a housing of the modular head assembly of FIG. 1B.
Figure 3B:
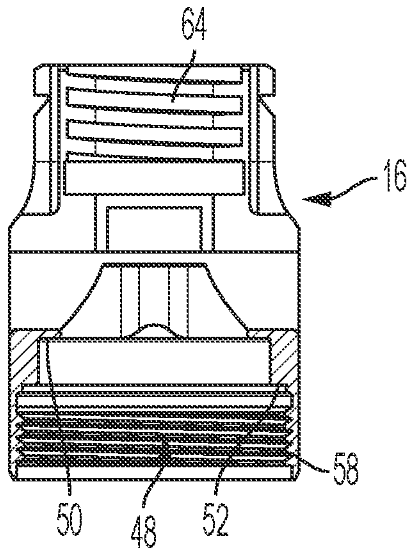
FIG. 3B is a cross section view of the housing of FIG. 3A taken along line 3B-3B.
Figure 3C:
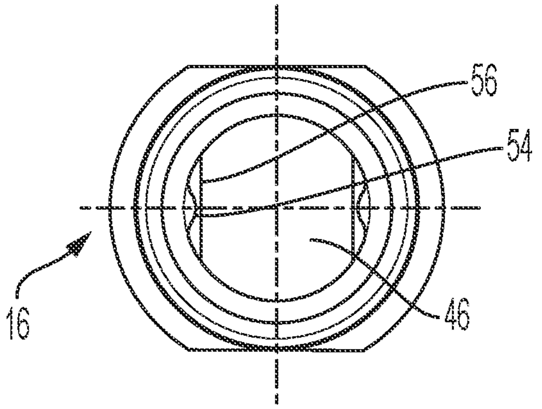
FIG. 3C is a bottom elevation view of the housing of FIGS. 3A and 3B.

Turning now to FIGS. 3A-3C, housing 16 has a generally cylindrical body with a proximal surface 42 and an opposite distal surface 44. Housing 16 defines a throughhole 46 extending along a longitudinal axis L of the body and between the proximal and distal surfaces of the housing.

The distal surface 44 of housing 16 defines a counterbore 48 that extends towards the proximal surface 42 of the housing and forms a first, or proximal annular face 50, and a second, or distal annular face 52. As shown in FIG. 3C, the sidewall delineating throughhole 46 is provided with a pair of longitudinally extending rails 54 in juxtaposed relationship to one another. Each rail 54 terminates at a stop 56 and is sized to be received within a portion of anvil 18, thereby enabling the anvil to slidably translate along the length of the rail and inhibiting the anvil from rotating within throughhole 46. An inner sidewall, forming a distal portion of counterbore 48, defines an internal threading 58 for securing the assembly cap 28 to housing 16.

Figure 12A:
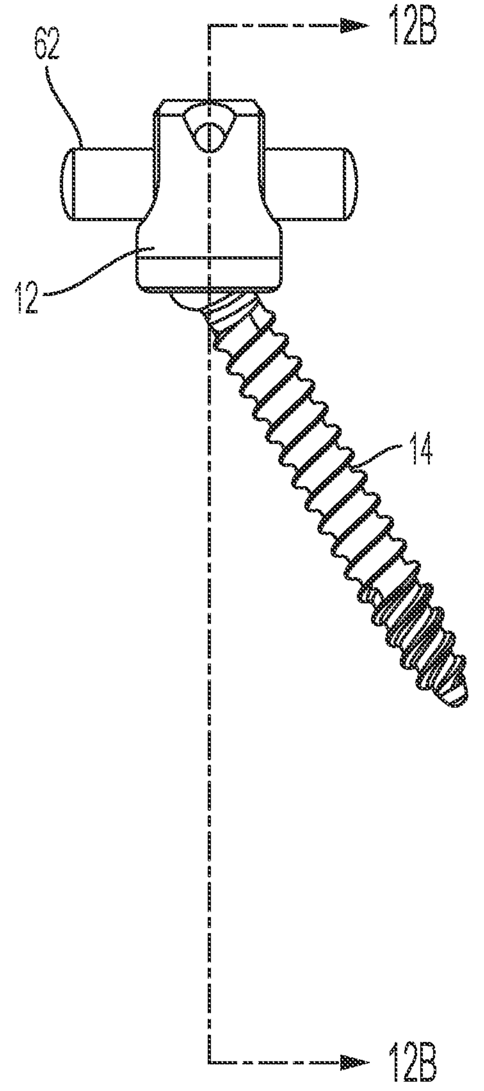
FIG. 12A is a side elevation view of an assembled spinal fixation device including a spinal rod, a set screw and the pedicle screw of FIG. 1A.
Figure 12B:
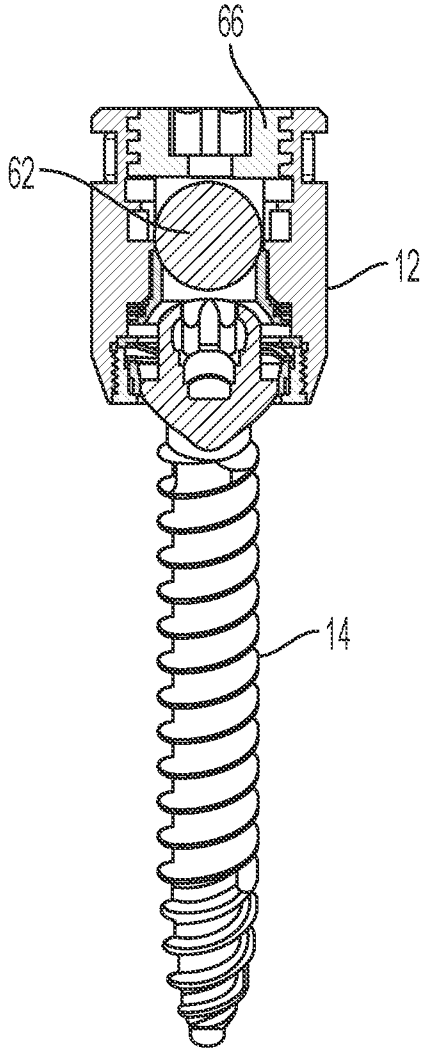
FIG. 12B is a cross section view of the spinal fixation device of FIG. 12A taken along line 12B-12B.

An outer surface of housing 16 defines a U-shaped opening 60 extending through the proximal surface 42 of the body in a transverse direction to throughhole 46. U-shaped opening 60 is sized and shaped to receive a spinal rod 62 (FIGS. 12A and 12B). As shown in FIG. 3B, an inner sidewall delineating a proximal portion of throughhole 46 defines an internal threading 64 for threadably receiving a set screw 66 (FIG. 12B) and securing spinal rod 62 within the U-shaped opening 60 of housing 16. Two reliefs 68 are formed in the outer surface of housing 16. The reliefs 68 are configured to receive a suitable tool (not shown) and enable a clinician to grasp and manipulate housing 16 during a surgical procedure. Housing 16 may be formed from any biocompatible material suitable for use in surgical procedures, such as metallic materials including titanium, titanium alloys, stainless steels, cobalt chrome alloys, etc., or non-metallic materials such as ceramics, polyetheretherketone (PEEK), etc.

Figure 4A:
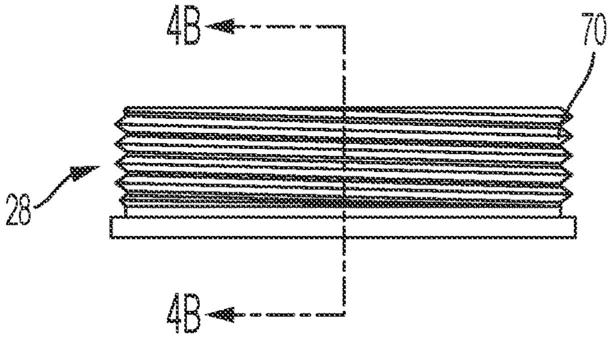
FIG. 4A is a side elevation view an assembly cap of the modular head assembly of FIG. 1B.
Figure 4B:
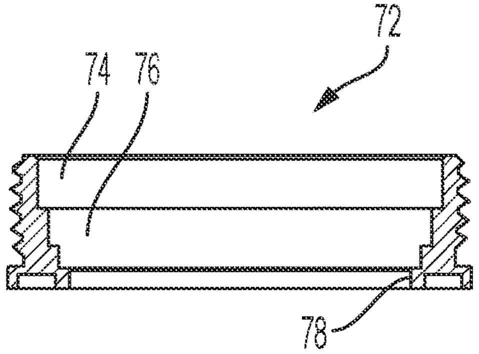
FIG. 4B is a cross section view of the assembly cap of FIG. 4A taken along line 4B-4B.

Assembly cap 28, shown in FIGS. 4A and 4B, includes an external threading 70 configured to threadably engage the internal threading 58 of housing 16 to assemble modular head assembly 12. With specific reference to FIG. 4B, an interior surface of assembly cap 28 defines a cavity 72 for receiving retaining ring 26. The cavity 72 of assembly cap 28 is formed by a sidewall defining a first portion 74 (proximal portion) having a first diameter and a second portion 76 (distal portion) having a second diameter smaller than the first portion. It is contemplated that the sidewall may be formed by multiple counterbores, as shown in FIG. 4B, an inward taper, or a combination of the foregoing. As will be described in further detail hereinbelow, the cavity 72 of assembly cap 28 is thus sized to allow retaining ring 26 to expand when the retaining ring is positioned within the first portion 74 (proximal portion) of the assembly cap and to compress the retaining ring about bone screw 14 when the retaining ring is positioned within the second portion 76 (distal portion) of the assembly cap. The distal end of assembly cap 28 may be provided with an inwardly projecting ledge 78 to limit the distal movement of retaining ring 26 and, in turn, prevent bone screw 14 from passing distally through modular head assembly 12 after the screw has been received therein.

Figure 5A:
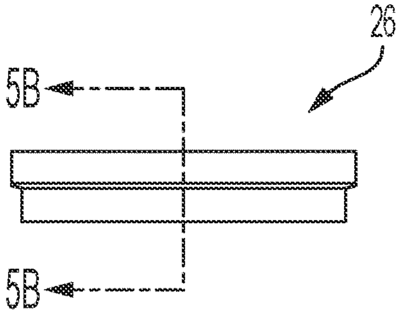
FIG. 5A is a side elevation view of a retaining ring of the modular head assembly of FIG. 1B
Figure 5B:
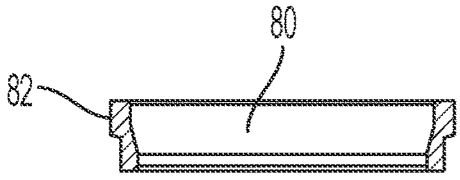
FIG. 5B is a cross section view of the retaining ring of FIG. 5A taken along line 5B-5B.
Figure 5C:
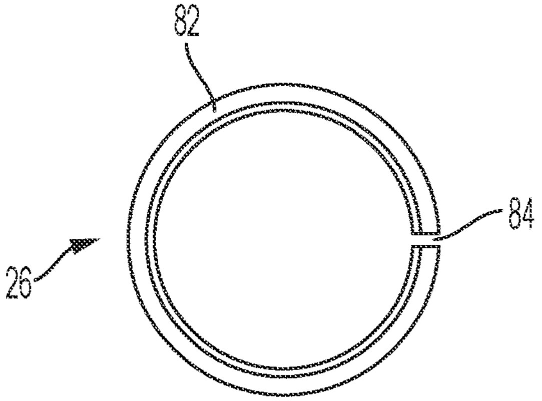
FIG. 5C is a top elevation view of the retaining ring of FIGS. 5A and 5B.

Referring to FIGS. 5A-5C, retaining ring 26 has a substantially ring shaped body, which defines a lumen 80 therethrough, and is sized to be moveably received within the cavity 72 of assembly cap 28. Retaining ring 26 includes a shelf 82 extending in radially outward direction about a proximal portion of the body. Shelf 82 has a relatively flat upper surface for engaging second biasing member 24 as retaining ring 26 translates within the cavity 72 of assembly cap 28. Retaining ring 26 is formed of an elastic material, such as an elastic metal, and defines a slit 84 extending through an outer surface of the ring shaped body and into communication with lumen 80. In this manner, retaining ring 26 is configured to compress upon the application of an external force (e.g., a compressive force applied to an outer surface of the body) and to expand upon the application of an internal force (e.g., an expansion force applied to an inner surface of the body). In this regard, retaining ring 26 is designed to transition between a neutral (or unexpanded configuration), an expanded configuration in which the retaining ring is sized to receive the head 30 of bone screw 14, and a compressed configuration in which the retaining ring prevents the head of the bone screw from passing distally through the retaining ring.

Figure 6A:
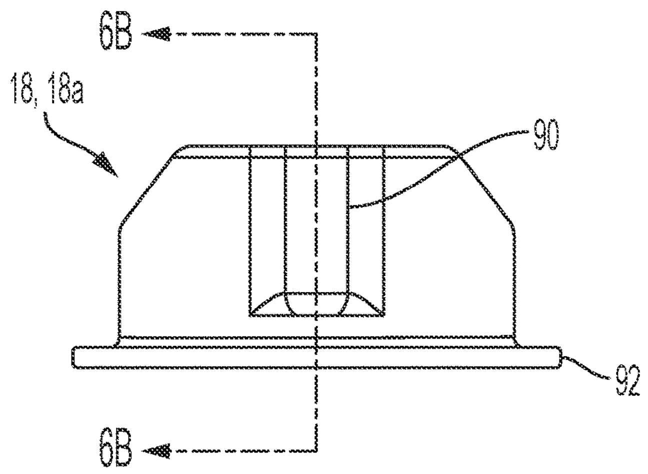
FIG. 6A is a side elevation view of a polyaxial anvil of the modular head assembly of FIG. 1B.
Figure 6B:
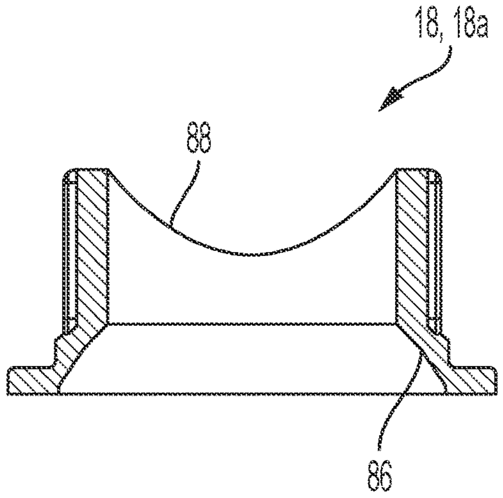
FIG. 6B is a cross section view of the polyaxial anvil of FIG. 6A taken along line 6B-6B.
Figure 6C:
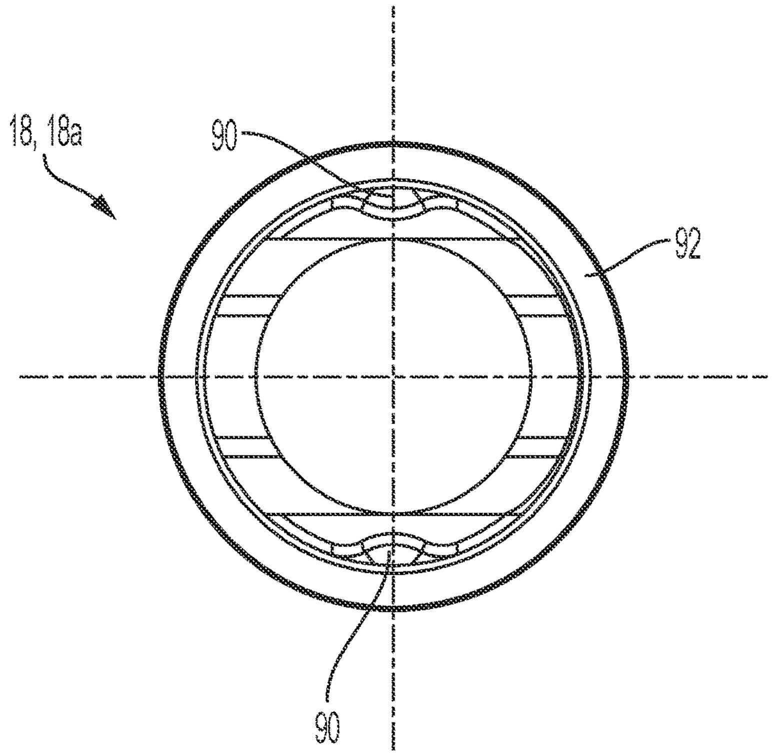
FIG. 6C is a bottom elevation view of the polyaxial anvil of FIGS. 6A and 6B.

As shown in FIGS. 6A-6C, polyaxial anvil 18*a* has a body defining a distal surface 86 and a proximal surface 88 and is sized to slide within a portion of the throughhole 46 of housing 16. The distal surface 86 of polyaxial anvil 18*a* defines a concave profile (e.g., extending toward the proximal surface 88 of the anvil). The concave profile of the distal surface 86 is generally spherical in shape, thereby allowing modular head assembly 12 to freely rotate in multiple directions about the head 30 of bone screw 14. The proximal surface 88 of polyaxial anvil 18*a* defines a concave profile (e.g., extending toward the distal surface 86 of the body) configured to receive a portion of spinal rod 62 (FIGS. 12A and 12B). A circumferential sidewall extending between the proximal and distal surfaces of polyaxial anvil 18*a* defines a pair of grooves 90 on opposite sides of the body. Each one of the grooves 90 extends in the longitudinal direction and is sized to receive a corresponding rail 54 of housing 16 to guide the sliding movement of polyaxial anvil 18*a* within throughhole 46 and to inhibit rotation of the anvil relative to the housing. In this manner, engagement between the rails 54 of housing 16 and the grooves 90 of anvil 18*a* ensures that the profiled proximal surface 88 of the anvil remains aligned with the U-shaped opening 60 of the housing to assist in properly aligning spinal rod 62 relative to modular head assembly 12.

The body of polyaxial anvil 18*a* also includes an outwardly extending flange 92 circumscribing a distal end of the body forming a seat to receive first biasing member 20. The bottom surface of flange 92 may be substantially flat and configured to engage washer 22.

Figure 7A:
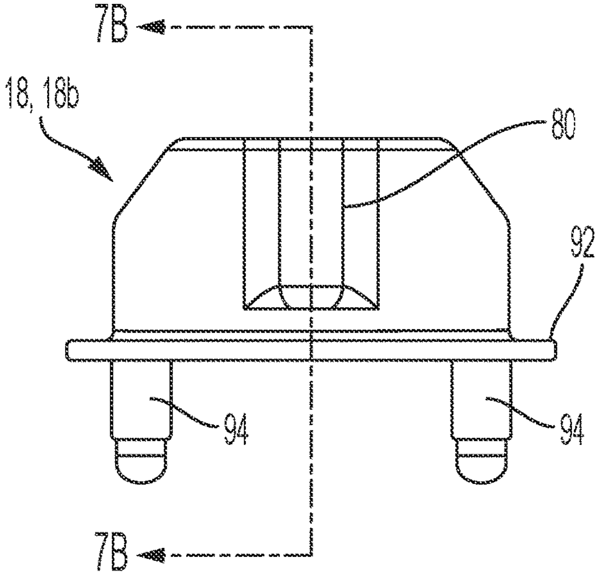
FIG. 7A is a side elevation view of a uniplanar anvil of the modular head assembly of FIG. 1B.
Figure 7B:
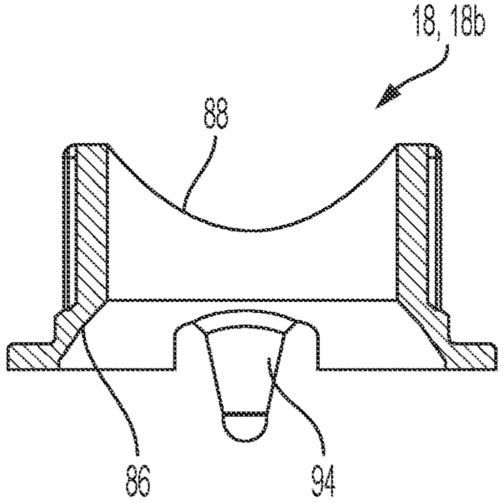
FIG. 7B is a cross section view of the uniplanar anvil of FIG. 7A taken along line 7B-7B.
Figure 7C:
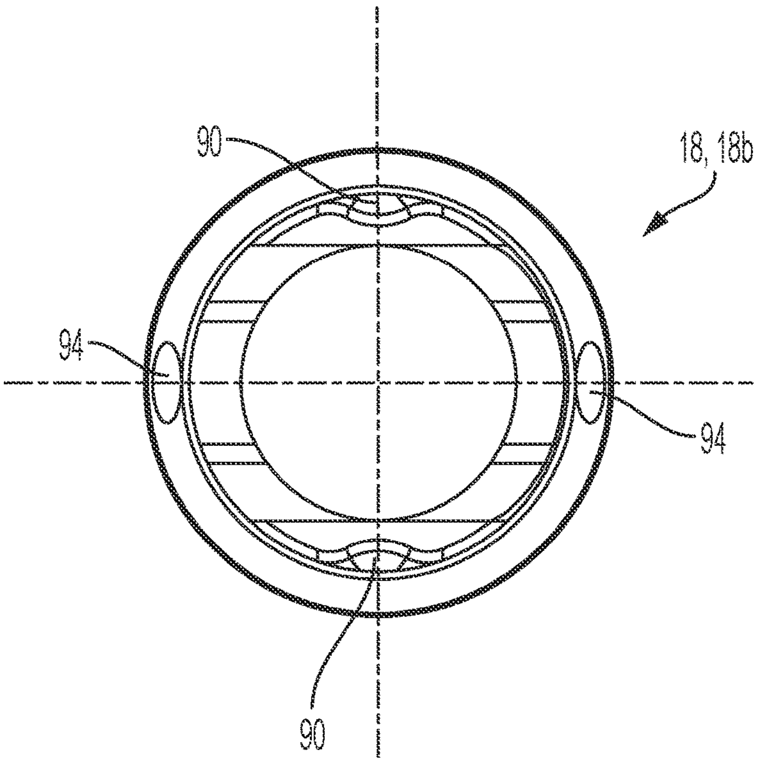
FIG. 7C is a bottom elevation view of the uniplanar anvil of FIGS. 7A and 7B.

Uniplanar anvil 18*b*, as shown in FIGS. 7A-7C, is substantially similar to polyaxial anvil 18*a* except that the uniplanar anvil additionally includes at least one protrusion 94. For example, uniplanar anvil 18*b* may include a pair of protrusions 94 extending in a longitudinal direction to a location distal of flange 92. As shown in FIGS. 7A and 7C, protrusions 94 may be circumferentially spaced about the anvil 180 degrees from one another with each protrusion circumferentially disposed between adjacent grooves 90. Protrusions 94 are sized and shaped to be positioned within the notch(es) 38 of bone screw 14. As previously mentioned, the cooperation between the protrusions 94 of uniplanar anvil 18*b* and the head 30 of bone screw 14 restricts movement of modular head assembly 12 to a single plane relative to the bone screw (e.g., the midplane between the protrusions).

Figure 8A:
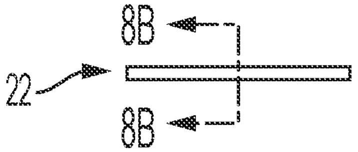
FIG. 8A is a side elevation view of a washer of the modular head assembly of FIG. 1B.
Figure 8B:
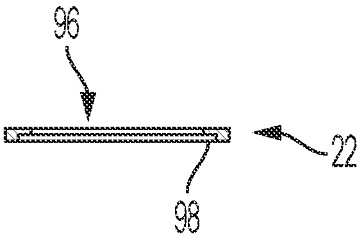
FIG. 8B is a cross section view of the washer of FIG. 8A taken along line 8B-8B.

Referring to FIGS. 8A and 8B, washer 22 has a ring shaped body. The body of washer 22 has a diameter smaller than the diameter of the portion of counterbore 48 located distal to the second (distal) annular face 52 and a diameter greater than the diameter of the portion of the counterbore located proximal to the second (distal) annular face. The second annular face is thus configured to prevent movement of washer 22 in a proximal direction when a proximal force is applied to the washer, for example, when bone screw 14 is loaded through the bottom surface of modular head assembly 12. The ring shaped body of washer 22 defines a proximal surface, a distal surface, and an aperture 96 extending therethrough to allow the head 30 of bone screw 14 to pass through the body of the washer when the bone screw is uploaded into housing 16. A notch 98 is positioned adjacent aperture 96. The notch 98 extends from the distal surface of washer 22 toward the proximal surface of the washer and forms a seat to receive second biasing member 24.

Figure 9:
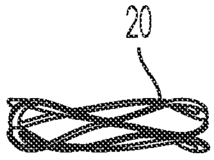
FIG. 9 is a side elevation view of a first wave spring of the modular head assembly of FIG. 1B.
Figure 10:
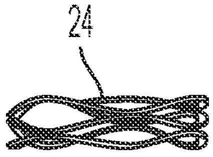
FIG. 10 is a side elevation view of a second wave spring of the modular head assembly of FIG. 1B.

As shown in FIG. 9, first biasing member 20 may be a spring, such as a wave spring, configured to entirely circumscribe the outer surface of anvil 18. When modular head assembly 12 is assembled, the first wave spring is slightly compressed between the first (proximal) annular face 50 of housing 16 and the flange 92 of anvil 18. Second biasing member 24, shown in FIG. 10, may also be a spring, such as a wave spring, sized to be received within the notch 98 of washer 22. As a result, when the head 30 of bone screw 14 is bottom loaded into modular head assembly 12, each of the first and second springs impart biasing forces to the bone screw at certain points of the loading process as is further explained hereinafter. These biasing forces ensure that the distal surface 86 of anvil 18 applies a constant distally directed force against the head of the bone screw to prevent modular head assembly 12 from "flopping" loosely about the head of the screw. In this manner, the biasing force affords the clinician greater control while securing modular head assembly 12 to bone screw 14.

Irrespective of whether modular head assembly 12 encompasses a polyaxial anvil 18*a* or a uniplanar anvil 18*b*, the modular head assembly is assembled in the same manner. For this reason, the following description of the assembly process refers to the anvil generically as anvil 18.

Modular head assembly 12 may be assembled by a manufacturer or an end user. To assemble modular head assembly 12, the first biasing member 20 is slid, in a proximal to distal direction, around anvil 18 until the biasing member is seated against flange 92. A user may then insert anvil 18 through the distal surface 44 of housing 16 while aligning the rails 54 of the housing and the grooves 90 of the anvil before sliding the anvil proximally along the rails of the housing until first biasing member 20 engages the first (proximal) annular face 50 of counterbore 48. Washer 22 may then be introduced into counterbore 48 until the proximal surface of the washer engages the second (distal) annular face 52 of housing 16. Next, second biasing member 24 is seated within the notch 98 of washer 22 and retaining ring 26 is inserted into the cavity 72 of assembly cap 28. The external threading 70 of assembly cap 28 may then be threaded into the internal threading 58 of housing 16 to threadably secure the assembly cap to the housing and, in turn, to secure washer 22 against the second (distal) annular face 52 of housing 16, and anvil 18, first biasing member 20, washer 22, second biasing member 24, and retaining ring 26 within the housing. In this regard, a manufacturer can assemble modular head 12 before shipping the modular head to the end user, or alternatively, an end user could assemble the modular head before surgery.

It will be appreciated, however, that assembly cap 28 may be secured to housing 16 via welding or any other known coupling mechanism.

Use of pedicle screw assembly 10 to fixate spinal rod 62 will now be described with reference to FIGS. 11A-12B. The surgeon may first evaluate the desired placement of spinal rod 62 and determine the desired type(s) of modular head assemblies (polyaxial or uniplanar) best suited for the operation. Because a polyaxial modular head assembly (containing a polyaxial anvil 18*a*) is secured to bone screw 14 in substantially the same manner in which a uniplanar modular head assembly (containing a uniplanar anvil 18*b*) is secured to the bone screw, a single generic description of the coupling will be described hereinafter such that specific descriptions pertaining to the polyaxial and uniplanar components are only set forth when describing contrasting features between the modular head assemblies.

Figure 11A:
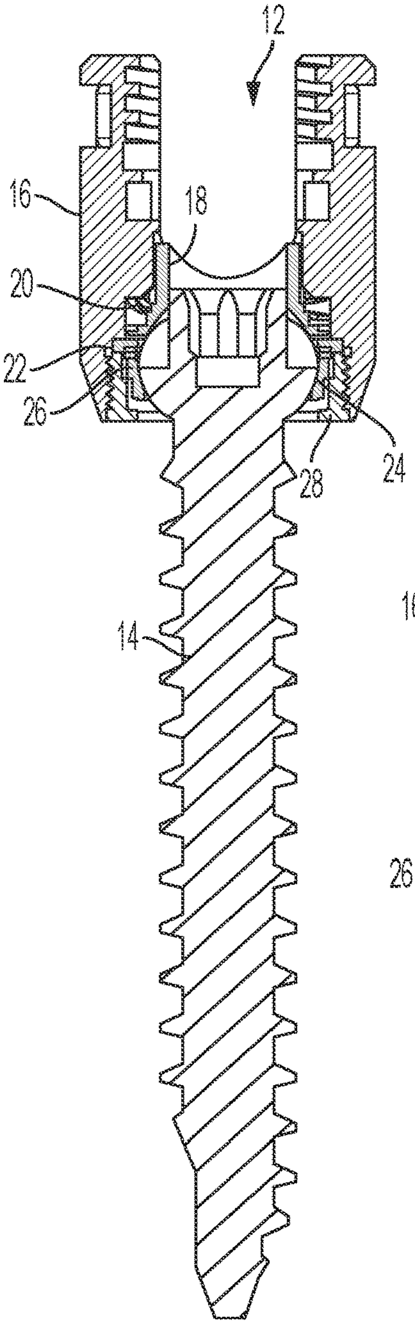
FIGS. 11A-11C are cross section views illustrating the bone screw of FIGS. 2A and 2B being bottom loaded into the modular head assembly of FIG. 1B.

Bone screw 14 is first driven into bone using a driving tool (not shown) by inserting a working end of the driving tool into the tool engaging recess 40 of the head 30 and rotating the driving tool to thread the screw into bone. With bone screw 14 secured at a desired location, modular head assembly 12 may be placed adjacent the head 30 of bone screw 14 and advanced in a distal direction over the head of the screw. With reference to FIG. 11A, as the head 30 of bone screw 14 is advanced proximally within throughhole 46, the head of the bone screw contacts retaining ring 26 and forces the retaining ring in a proximal direction. More particularly, retaining ring 26 compresses second biasing member 24 between washer 22 and the retaining ring as the retaining ring translates in a proximal direction from the distal portion 76 of assembly cap 28 into the proximal portion 74 of the assembly cap. When the head 30 of bone screw 14 applies an outwardly directed force on retaining ring 26, the resilient retaining ring transitions from the neutral (or unexpanded) configuration to the expanded configuration. Retaining ring 26 is permitted to expand to the expanded configuration, in part, because the retaining ring is disposed within the larger proximal portion 74 of assembly cap 28.

Figure 11B:
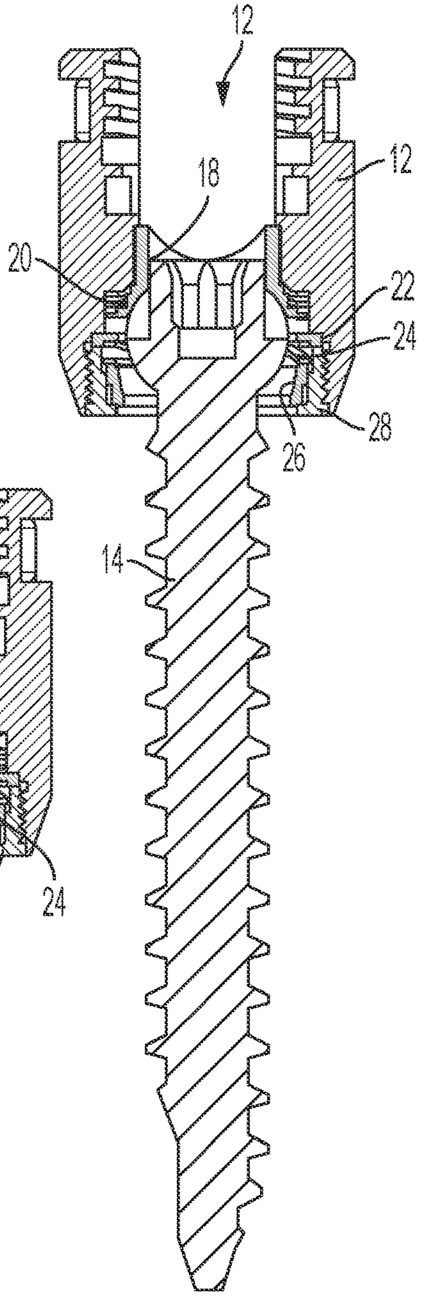
Figure 11C:
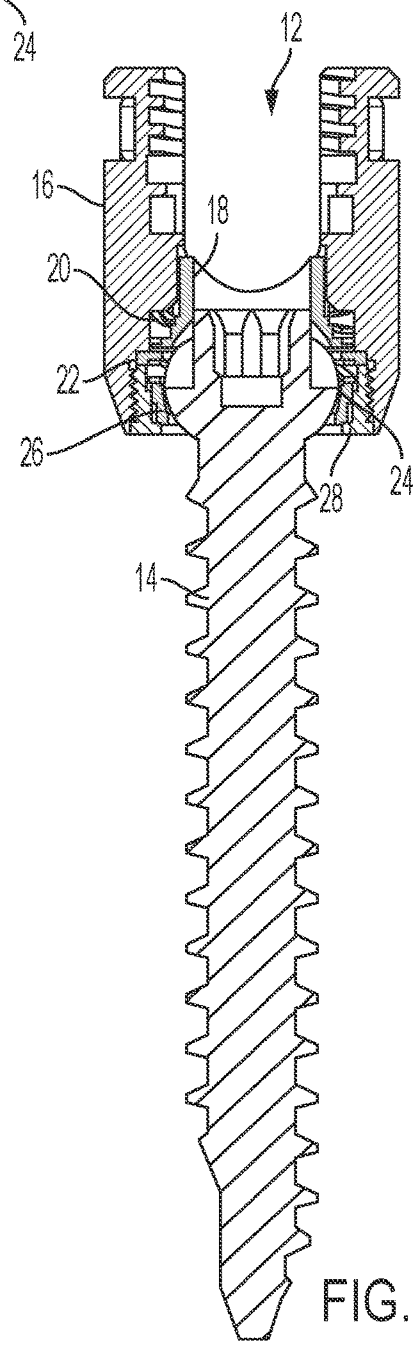

As shown in FIG. 11B, further movement of the modular head assembly 12 in a distal direction relative to bone screw 14, causes the head 30 of the bone screw to pass completely through the lumen 80 of retaining ring 26 and the aperture 96 of washer 22 and into the contact with the distal surface 86 of anvil 18, thereby causing the anvil to translate proximally within the throughhole 46 of housing 16 which, in turn, compresses the first biasing member 20 between the first (proximal) annular face 50 of the housing and the flange 92 of the anvil. The cooperation between the rails 54 of housing 16 and the grooves 90 of anvil 18, guides the proximal movement of the anvil within throughhole 46 until the proximal surface 88 of the anvil engages stop 56.

Once the head 30 of bone screw 14 has passed completely through retaining ring 26, the retaining ring will elastically return to its neutral or unexpanded size. The second biasing member 24 will then immediately force retaining ring 26 toward the distal surface 44 of housing 16 and into the second (distal) portion 76 of assembly cap 28 causing the retaining ring to transition from the neutral (unexpanded) configuration to the compressed configuration. It will be appreciated that the biasing force provided by second biasing member 24 is independent of first biasing member 20. More specifically, washer 22 isolates the forces provided by first biasing member 20 and second biasing member 24, respectively. In this regard, after the head 30 of bone screw 14 has passed through retaining ring 26 and washer 22, second biasing member 24 forces the retaining ring 26 into the smaller distal portion 76 of assembly cap 28 and compresses the retaining ring, thereby preventing the head of the bone screw from passing distally through the retaining ring regardless of the manipulation techniques used by the clinician. Put differently, without washer 22 isolating second biasing member 24, some manipulation techniques could cause retaining ring 26 to move proximally within the throughhole 46 of housing 16 (via contact with the bone screw) thereby transitioning the retaining ring back to the neutral confirmation making the head 30 of bone screw 14 susceptible to passing distally through the retaining ring.

With the head 30 of bone screw 14 pressed against the distal surface 86 of anvil 18, first biasing member 20 provides a constant biasing force to the head of the bone screw. The constant force prevents modular head assembly 12 from "flopping" loosely about the head 30 of bone screw 14. As a result, the orientation and position of modular head assembly 12, relative to bone screw 14, is not altered unless the clinician intentionally applies a meaningful rotational force to the modular head assembly. The biasing force thus affords the clinician greater control and the ability to make minor adjustments in the position of the modular head assembly relative to the screw. With specific reference to FIG. 11C, after modular head assembly 12 has been positioned by the clinician and has been released, the first biasing member 20 urges anvil 18 in a distal direction causing the anvil to slide along the rails 54 of housing 16 toward washer 22. At the same time, anvil 18 forces the head 30 of bone screw 14 in the distal direction which, in turn, moves retaining 26 further into the distal portion 76 of assembly cap 28 which further compresses the retaining ring around the head of the bone screw and locks the bone screw within housing 16.

If modular head assembly 12 encompasses a polyaxial anvil 18*a*, the substantially spherical head 30 of bone screw 14 will permit the concave distal surface 86 of the polyaxial anvil to rotate about the head in multiple directions, thereby allowing the surgeon to adjust the position of modular head assembly relative the bone screw in multiple axis. In contrast, if modular head assembly 12 encompasses a uniplanar anvil 18*b*, the protrusion(s) 94 of the uniplanar anvil will be positioned within notches 38 of bone screw 14, thereby restricting the clinician's ability to adjust the modular head assembly relative to the bone screw to a single axis.

Referring now to FIGS. 12A and 12B, spinal rod 62 may then be interconnected between adjacent modular head assemblies 12 by inserting the spinal rod within the U-shaped openings 60 of each housing 16 and within a concave relief of a respective proximal surface 88 of an anvil 18. Again, the biasing force imparted by first biasing member 20 will prevent each modular head assembly 12 from rotating relative to its respective bone screw 14 during placement of the spinal rod 62 (e.g., as a result of gravitations forces and/or minor forces imparted by the rod itself) while the biasing forces imparted by first biasing member 20 and second biasing member 24 secure retaining ring 26 within the second (distal) portion 76 of assembly cap 28, preventing the head of the bone screw from passing distally through the retaining ring and the distal surface 44 of housing 16. With spinal rod 62 properly positioned between modular head assemblies 12, the surgeon may then use a driving tool to thread set screw 66 into the threads 64 of housing 16, which in turn, secures the flange 92 of anvil 18 against washer 22 and prevents the anvil from translating proximally within the throughhole 46 of housing 16.

Figure 13A:
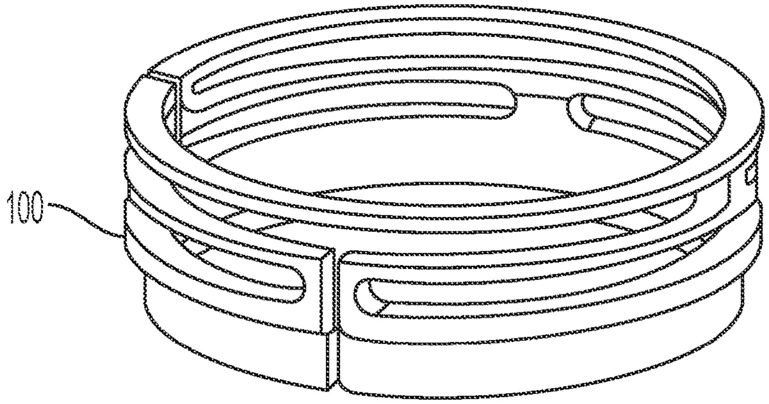
FIGS. 13A-13C are perspective, side elevation, and cross section views, respectively, of a variant retaining ring for use in a variant modular head assembly.
Figure 13B:
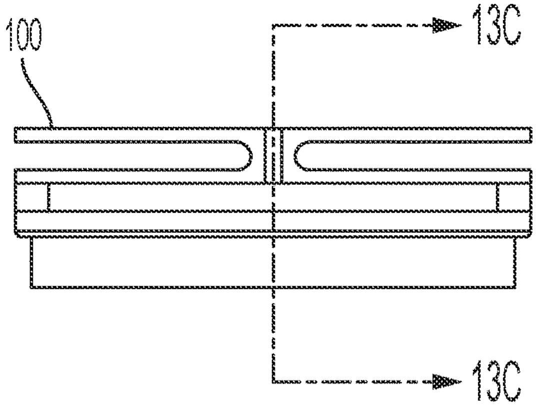
Figure 13C:
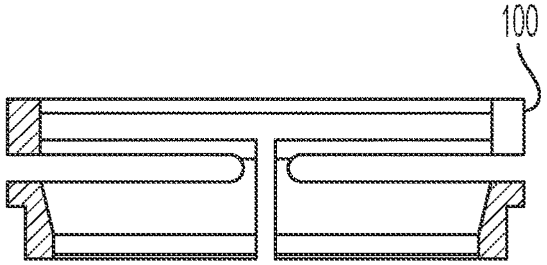
Figure 14A:
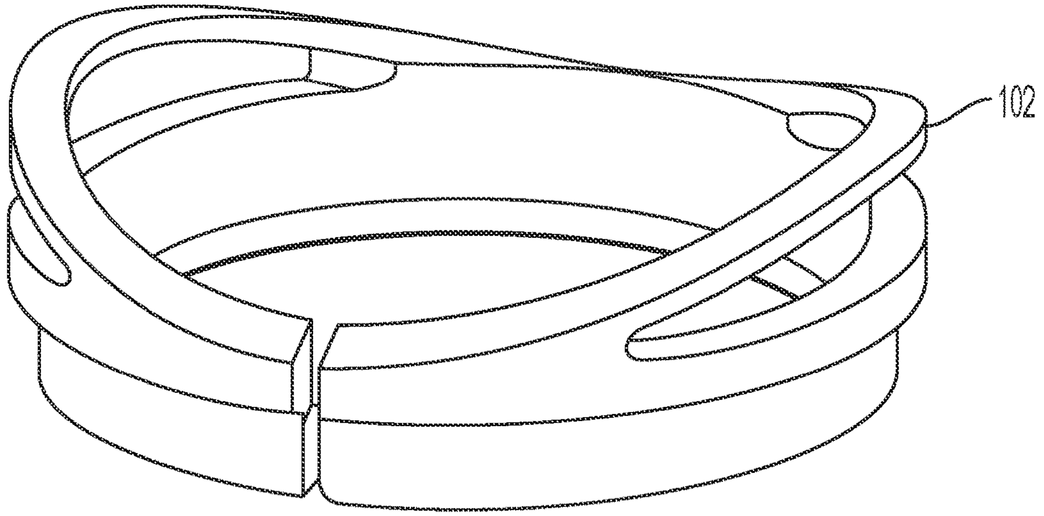
FIGS. 14A-14C are perspective, side elevation, and cross section views, respectively, of another variant retaining ring for use in another variant modular head assembly.
Figure 14B:
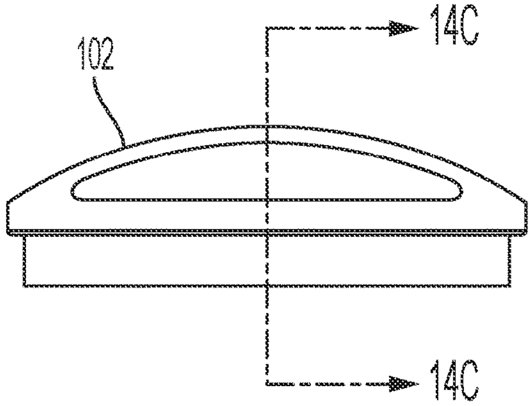
Figure 14C:
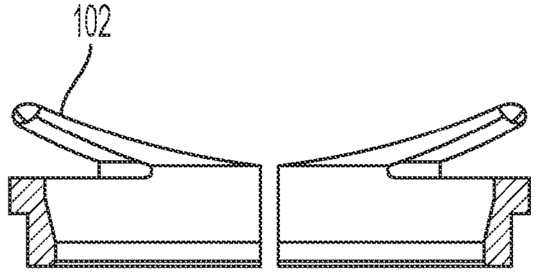

Variant modular head assemblies are also described herein. The variant modular head assemblies includes all of the components of modular head assembly 12 except that the variant modular head assemblies includes variant retaining rings that replace retaining ring 26 and second biasing member 24 of modular head assembly 12. For example, variant retaining ring 100 (FIGS. 13A-13C) and variant retaining ring 102 (FIGS. 14A-14C) are monolithic components (e.g., a single component) formed substantially the same as retaining ring 26, described above and illustrated in FIGS. 5A-5C, and further including a biasing member extending from the shelf located at the proximal end of the retaining ring. With specific reference to FIGS. 13A-13C, the biasing member may be a coiled spring substantially or partially circumscribing its circumferential wall. Alternatively, as shown in FIGS. 14A-14C, the biasing member may be one or more wave springs, which individually or collectively, circumscribe its circumferential wall. It is contemplated, however, that other retaining rings may be formed with other springs or other biasing members. Monolithic retaining ring 100 and monolithic retaining ring 102 facilitate efficient assembly of the variant modular head assembly (e.g., the monolithic retaining ring can be loaded into the housing without requiring that second biasing member 24 and retaining 26 of modular head assembly 12 be loaded separately into housing 16). The variant modular head assemblies are otherwise assembled and used during surgery as described above with respect to modular head assembly 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal fixation device, comprising:

a bone screw including head and a shank extending from the head; and a modular head assembly, comprising:

a housing having a proximal surface, a distal surface, and a throughhole formed through the housing from the proximal surface to the distal surface;

an anvil slidable within a portion of the throughhole;

a washer disposed within the throughhole of the housing, the washer having a proximal surface, a distal surface, and an aperture extending through the washer from the proximal surface to the distal surface, the aperture sized to receive the head of the bone screw therethrough;

an assembly cap secured to the housing, the assembly cap including an inner surface defining a cavity having a first portion and a second portion, the first portion having a first diameter and the second portion having a second diameter smaller than the first diameter;

a first biasing member arranged to bias the anvil toward the proximal surface of the washer;

a retaining ring positioned at least partially within the cavity of the assembly cap, the retaining ring transitionable between a first configuration in which the retaining ring is sized to receive the head of the bone screw and a second configuration in which the retaining ring is compressed about the bone screw; and a second biasing member formed monolithic with the retaining ring and arranged to bias the retaining ring toward the second portion of the assembly cap by providing a spring force toward the second portion, wherein movement of the retaining ring from the first portion of the assembly cap to the second portion of the assembly cap compresses the retaining ring from the first configuration to the second configuration and secures the bone screw relative to the housing.

2. The spinal fixation device of claim 1, wherein a distal portion of the housing defines a counterbore terminating at a first annular face.

3. The spinal fixation device of claim 2, wherein the anvil defines a proximal end, a distal end and a circumferential sidewall extending therebetween, the distal end of the anvil comprising an outwardly extending flange.

4. The spinal fixation device of claim 3, wherein the first biasing member surrounds the circumferential sidewall of the anvil and is biased between the first annular face and the outwardly extending flange of the anvil.

5. The spinal fixation device of claim 1, wherein the retaining ring defines a proximal end and a distal end, the proximal and distal ends of the retaining ring defining a lumen therethrough.

6. The spinal fixation device of claim 5, wherein the retaining ring is formed from a resilient material, and wherein an outer surface of the retaining ring defines a slit in communication with the lumen.

7. The spinal fixation device of claim 5, wherein the second biasing member is biased between the washer and the proximal surface of the retaining ring.

8. The spinal fixation device according to claim 1, wherein at least one of the first biasing member or the second biasing is a wave spring.

9. The spinal fixation device of claim 1, wherein the housing defines a threading and the assembly cap includes a corresponding threading configured to threadably secure the assembly cap to the housing.

10. The spinal fixation device of claim 1, wherein the inner surface of the assembly cap includes an inwardly extending ledge at a distal end of the assembly cap to limit distal movement of the retaining ring.

11. The spinal fixation device of claim 1, wherein the head of the bone screw defines at least one notch.

12. The spinal fixation device of claim 11, wherein the at least one notch comprises first and second notches on opposite sides of the head of the bone screw.

13. A method of assembling a modular head assembly, comprising:

providing a housing having a proximal portion adjacent a proximal surface, a distal portion adjacent a distal surface, and a throughhole formed through the housing from the proximal surface to the distal surface defining first and second annular faces;

sliding an anvil into the throughhole to bias a first biasing member between the first annular face and a portion of the anvil;

placing a washer within the throughhole such that the washer is located distal of the anvil;

inserting a resilient retaining ring having a monolithically formed second biasing member at least partially into an assembly cap, the assembly including an inner surface defining a cavity having a first portion with a first diameter and a second portion with a second diameter smaller than the first diameter; and securing the assembly cap to the housing, thereby fixing the washer against the second annular face and compressing a second biasing member to bias the retaining ring toward the second portion of the assembly cap by providing a spring force toward the second portion.

14. The method of claim 13, further comprising positioning the first biasing member around the anvil prior to or during the sliding step.

15. The method of claim 13, wherein the securing step comprises threadably engaging threading on the assembly cap with corresponding threading on the housing.

* * * * *